US006585658B2

United States Patent
Redaelli et al.

(10) Patent No.: US 6,585,658 B2
(45) Date of Patent: Jul. 1, 2003

(54) SYSTEM AND METHOD FOR THE AUTOMATIC EVALUATION OF THE INDEXES OF VOLEMIC STATUS

(75) Inventors: Alberto Redaelli, Milan (IT); Monica Soncini, Milan (IT); Giuseppe Susini, Milan (IT)

(73) Assignee: Politecnico di Milano, Milan (IT)

( * ) Notice: Subject to any disclaimer, the term of this patent is extended or adjusted under 35 U.S.C. 154(b) by 26 days.

(21) Appl. No.: 09/854,490

(22) Filed: May 15, 2001

(65) Prior Publication Data

US 2001/0053881 A1 Dec. 20, 2001

(30) Foreign Application Priority Data

May 16, 2000 (IT) .................................. M12000A1070

(51) Int. Cl.$^7$ ................................................. A61B 5/02
(52) U.S. Cl. ........................ 600/484; 600/481; 600/502; 600/534
(58) Field of Search ................................ 600/481, 483, 600/484, 500, 502, 534, 535, 595

(56) References Cited

U.S. PATENT DOCUMENTS

| | | | | |
|---|---|---|---|---|
| 4,495,947 A | * | 1/1985 | Motycka | 128/205.14 |
| 4,953,556 A | * | 9/1990 | Evans | 128/671 |
| 5,520,192 A | * | 5/1996 | Kitney et al. | 128/716 |
| 6,398,739 B1 | * | 6/2002 | Sullivan et al. | 600/529 |

OTHER PUBLICATIONS

Pizov et al, "The Arterial Pressure Waveform During Acute Ventricular Failure and Synchronized External Chest Compression", Anesthesia and Analgesia, U.S., Feb. 1989, vol. 68, No., 2 Feb. 1989, pp. 150–156.

Priesman et al, "New Monitors of Intravascular vol.: A Comparison of Arterial Pressure Waveform Analaysis and the Intrathoracic Blood vol.", Intensive Care Medicine, U.S., Jun. 1997, vol. 23, No. 6, Jun. 1997, pp. 651–657.

* cited by examiner

Primary Examiner—Mark Paschall
(74) Attorney, Agent, or Firm—Nixon & Vanderhye, P.C.

(57) ABSTRACT

The present invention refers to a system and a method for the automatic evaluation of the indexes of volemic status (Systolic Pressure Variation or SPV) in patients submitted to mechanic ventilation, starting form the analysis of the variations of the values of blood pressure.

In one embodiment the system for the automatic evaluation of indexes of volemic status of a patient comprises: elements suitable for submitting said patient to a preset period of apnoea and to a preset period of mechanical breathing; heart pressure probes for acquiring an analogical signal relative to the values of the blood pressure of said patient in said preset periods; an analogue/digital converter for the conversion of said analogical signals into a digital signal; system for determining the values of positive systolic peaks of said pressure; element for determining a first average value of the positive systolic peaks of said pressure in said preset period of apnoea; element for determining a second average value of the maximum positive systolic peaks of said pressure in said preset period of mechanical breathing; element for determining a third average value of the minimum positive systolic peaks of said pressure in said preset period of mechanical breathing; system for calculating a first index of volemic status equal to the difference between said second value and said first value; system for calculating a second index of volemic status equal to the difference between said third value and said first value; a display of said indexes of volemic status.

13 Claims, 2 Drawing Sheets

SYSTEM AND METHOD FOR THE AUTOMATIC EVALUATION OF THE INDEXES OF VOLEMIC STATUS

The present invention refers to a system and a method for the automatic evaluation of the indexes of volemic status (Systolic Pressure Variation or SPV) in patients submitted to mechanical ventilation, starting from the analysis of blood pressure variations.

The system permits the acquisition of values of blood pressure from the transducers, to analyse said signals automatically and calculate the indexes of volemic status in seconds.

At present the indexes of volemic status is calculated starting from recordings of the pressure signal on graph paper, and carrying out operations of manual calculation, which require time and can lead to even significant errors.

The blood pressure signal is acquired following a pre-set clinical protocol, which provides for an interval of several seconds of apnoea and for an interval of several seconds of mechanical breathing.

In view of the state of the technique described, the object of the present invention is to provide for a system for the automatic evaluation of the indexes of volemic status capable of presenting the results in a very brief time and being highly precise, in addition being capable of giving an immediate warning or alarm indication in the event of values which are outside the interval.

In accordance with the present invention, said object is reached by means of a system for the automatic evaluation of indexes of volemic status of a patient comprising: means suitable for submitting said patient to a preset period of apnoea and a preset period of mechanical breathing; blood pressure probes for acquiring an analogue signal relative to the values of the blood pressure of said patient in said preset periods; an analogue/digital converter for converting said analogue signal into a digital signal; means for determining the values of the positive systolic peaks of said pressure; means for determining a first average value of the positive systolic peaks of said pressure in said preset period of apnoea; means for determining a second average value of the maximum positive systolic peaks of said pressure in said preset period of mechanical breathing; means for determining a third average value of the minimum positive systolic peaks of said pressure in said preset period of mechanical breathing; means for calculating a first index of volemic status equal to the difference between said second value and said first value; means for calculating a second index of volemic status equal to the difference between said third value and said first value; a display of said indexes of volemic status.

Said object is also reached by means of a method for the evaluation of the indexes of volemic status of a patient comprising the following phases: submitting said patient to a period of preset duration of apnoea; submitting said patient to a period of preset duration of mechanical breathing; acquiring the blood pressure values of said patient in said preset periods by suitable pressure probes; determining the values of the positive systolic peaks of said pressure; determining a first average value of the positive systolic peaks of said pressure in said period of apnoea; determining a second average value of the maximum positive systolic peaks of said pressure in said period of mechanical breathing; determining a third average value of the minimum positive systolic peaks of said pressure in said period of mechanical breathing; calculating a first index of volemic status equal to the difference between said second value and said first value; calculating a second index of volemic status equal to the difference between said third value and said first value; visualizing said indexes of volemic status on a display.

The characteristics and advantages of the present invention will appear evident from the following detailed description of an embodiment thereof, illustrated as non-limiting example in the enclosed drawings, in which.

Figure 1:
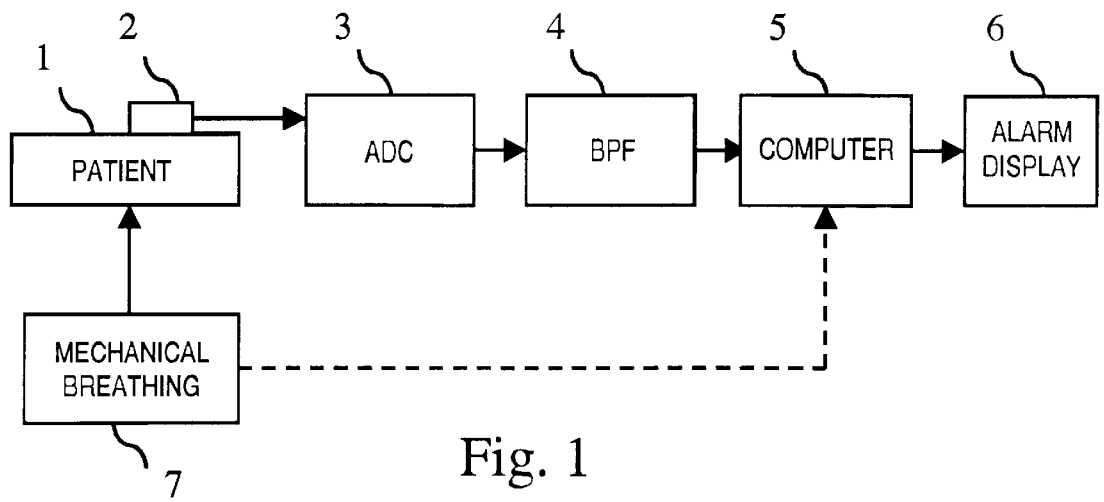
FIG. 1 represents a simplified block diagram of an example of an embodiment of the system for automatic evaluation of the indexes of volemic status in accordance with the present invention.

An example of an embodiment of the system for automatic evaluation of the indexes of volemic status in accordance with the present invention is shown in FIG. 1, wherein a patient 1 to whom a blood pressure probe 2 is associated is visualized very symbolically. The analogue signal produced by the probe 2 is placed in input to an analogue/digital converter 3. The signal is therefore preferably filtered with a band-pass filter 4, having a pass-band preferably between 0,5 and 30 Hz, and is sent to a computer 5, equipped with a suitable connection interface, used to elaborate the signal received. The filtering carried out by the filter 4 can also be carried out directly by the computer 5. An alarm signal display 6 is associated to computer 5. The means of mechanical breathing 7 are suitably connected to the patient 1, and a signal indicating the state of activation or deactivation of the same can be read from these and sent to computer 5.

The indexes of volemic status are evaluated on the basis of a predefined clinical protocol which provides for an interval of several seconds (for example 3 seconds) in which the mechanical breathing supplied by means 7 to patient 1 is suspended, therefore the patient is in a temporary situation of apnoea, and for another interval of several seconds (for example 20 seconds) of mechanical breathing. Preferably the period of apnoea precedes the period of mechanical breathing.

The heart pressure signal acquired in these two periods is supplied (after the analogue/digital conversion and the filtering) to computer 5, which carries out the elaborations.

Figure 2:
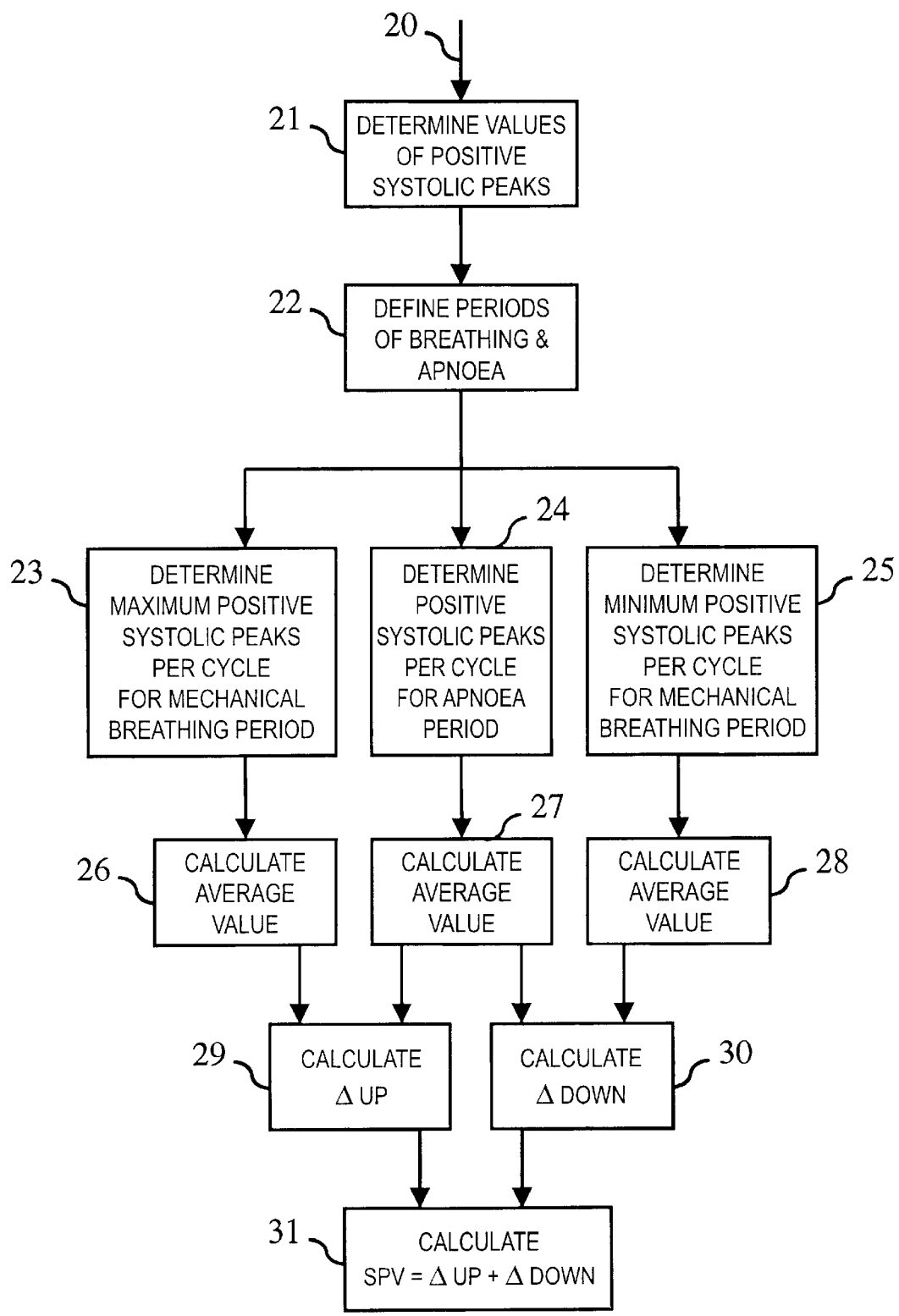
FIG. 2 represents a flow diagram for the calculation of the indexes of volemic status.

A flow diagram for the calculation of the indexes of volemic status is shown in FIG. 2. Computer 5 receives in input the digital signal 20. The values of the positive systolic peaks 21 of every heart cycle are determined. The two periods 22 of mechanical breathing and of apnoea are defined so as to divide into two groups, the values of the peaks, as mentioned above, for the successive operations. By positive systolic peak we mean the peak of pressure within a heart cycle. In the phase of mechanical breathing the positive systolic peaks have an undulatory flow and therefore it is possible to determine both the maximums and the minimums. In the phase of apnoea all the positive systolic peaks are considered.

The determination of the maximum positive systolic peaks 23 of every heart cycle relating to the period of mechanical breathing is made and the average value 26 is calculated.

The determination of the positive systolic peaks 24 of every heart cycle relating to the period of apnoea is made and the average value 27 is calculated.

The determination of the minimum positive systolic peaks 25 of every heart cycle relating to the period of mechanical breathing is made and the average value 28 is calculated.

A first index of volemic status 29 denominated Δup equal to the difference between the average value of the maximum positive systolic peaks of every heart cycle relating to the period of mechanical breathing and the average value of the positive systolic peaks of every heart cycle relating to the period of apnoea. are calculated A second index of volemic status 30 denominated Δdown equal to the difference between the average value of the minimum positive systolic peaks of every heart cycle relating to the period of mechanical breathing and the average value of the positive systolic peaks of every heart cycle relating to the period of apnoea are calculated.

Preferably, a third index of volemic status 31 denominated SPV is calculated as the sum of the index Δup and the index Δdown.

To determine the values of the positive systolic peaks 21 of every heart cycle, the signal is filtered by means of the filter 4, then the main frequency of the signal is determined and that is the heart frequency by means of the analysis of the spectrum in frequency of the signal and determining the frequency of the highest peak present in the spectrum of the interval between 0,5 and 3 Hz. The spectrum in frequency is, for example, determined carrying out a Fast Fourier Transform of the signal received. The number of points per heart cycle is then determined, which is calculated as a ratio between the sampling frequency of the analogue/digital converter and the main or heart frequency of the pressure signal. The peak values of the systolic pressure for every heart cycle are then determined. For the first cycle the peak is looked for in an amplitude window equal to the total number of the points per cycle or in other terms equal to the time amplitude of the heart cycle. For the successive cycles the research window is equal to a preset portion of the entire heart cycle and included between 0,1 and 1 time the number of points per heart cycle and preferable equal to a tenth (0,1) of the total number of the points per cycle and is centred starting from the position of the previous pressure peak and that is centred in the position given by the sum of the time position of the peak of the previous heart cycle plus a time amplitude of the heart cycle. The value of the peak of the systolic pressure to be looked for corresponds to the maximum value present inside the point window examined.

In a further embodiment, so as to avoid possible errors in the identification of the positive systolic peaks (as there is the possibility that the method incorrectly identifies a relative maximum of the cycle as a peak) proceed as follows. As the error that can occur is that a relative maximum of a much lower value is incorrectly confused with a positive systolic peak, as a first step (a) the values of the negative diastolic peaks of the pressure graph are calculated, suitably filtered with a 0.5–3 Hz pass-band, to eliminate all the relative maximums and minimums of the signal; as a second step (b) an average of these values is made; as a third step (c) a reference value is determined equal to the average value increased preferably by 10 mmHg. The value of mmHg of increase must be between zero and the difference between the average value of the positive systolic peaks and the average value of the negative diastolic peaks and anyway preferably of a value lower than 30 mmHg. Then a comparison is made between every single positive systolic peak previously determined within the initial preset amplitude window (equal to a tenth of the total number of the points per cycle) and the above mentioned reference value. If all the peak values determined exceed the reference value, the result is considered correct; if only one peak value is lower than the reference value, the result is rejected. In this case the operation is repeated with an increased amplitude window compared to the previous one, for example by 10%, that is the positive systolic peaks are determined again within the new window. The operation is repeated (up to 1000 times) until all the peaks of the graph exceed the reference value.

The identification of the two periods 22 of mechanical breathing and of apnoea can come about in various manners. In one embodiment an external operator suitably positioning some cursors can define the two intervals manually. Two cursors enable the identification of the time interval of the heart pressure to use as reference value (apnoea interval), two more cursors enable the identification of the time interval of the heart pressure to use as variation values (mechanical breathing interval). It is preferable to use four cursors instead of three cursors as in this manner it is possible to not consider parts of the pressure graph around the passing from apnoea to mechanical breathing which could have transitory phases that could alter the calculation of the indexes of volemic status.

In another embodiment the two intervals are preset on the basis of the preset protocol and are highlighted by means of suitable luminous or acoustic signals.

In a further embodiment the two intervals are defined automatically through the analysis of the progress of the graph of the systolic pressure peaks: that part of the graph that presents an almost constant flow belongs to the interval of apnoea, while the part of the signal that shows slope variations is part of the breathing interval. Or alternatively the means 7 supply the computer 5 with a signal indicating the state of activation or deactivation of the same mechanical breathing means 7.

Figure 3:
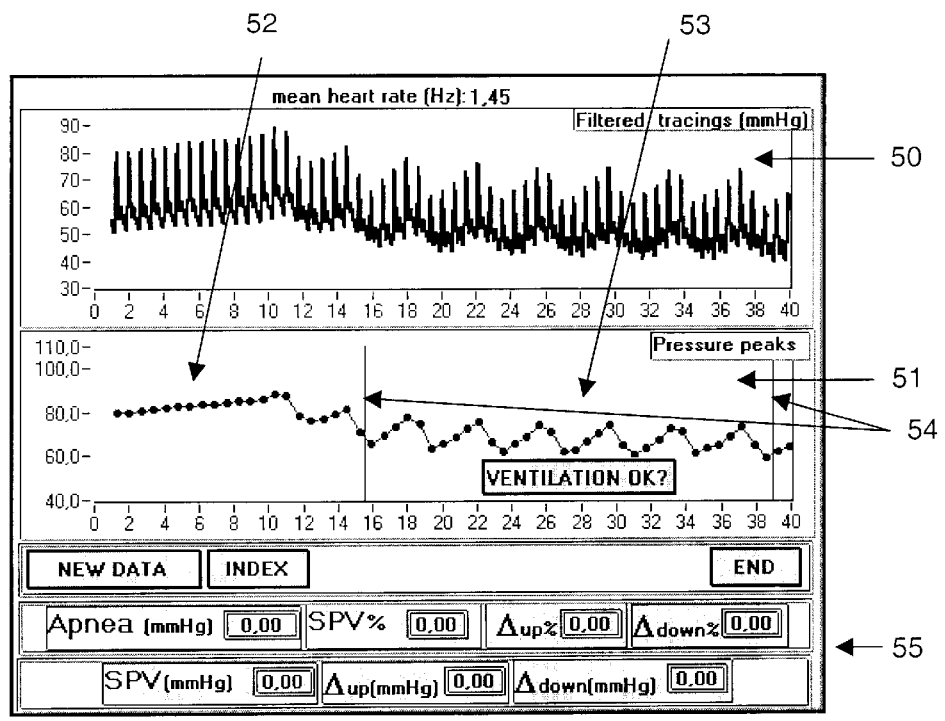
FIG. 3 represents an example of the visualization of the indexes of volemic status and of the heart graph.

In FIG. 3 an example of visualization of the indexes of volemic status and of the heart graph is shown, it is obvious that other forms of visualization are possible. In particular with the reference 50 a graph of the filtered signal of heart pressure is indicated and with the reference 51 the flow of the positive peaks identified starting from graph 50 is indicated. The indicators 54 visualized identify the part of the graph relative to artificial breathing 53, while the part with more constant flow indicates the part of the graph relative to the apnoea 52. In addition, the various indexes of volemic status 55 are indicated. In the case of values that are outside the normality interval said indices can be made to flash or other types of warning and/or alarm can be activated.

The system in accordance with the present invention can be constructed in various manners. The acquisition of the data from the sensors can be carried out directly by suitable instruments (already present in operating rooms) and the elaboration of the data can be carried out by a computer connected to them or by a microprocessor card inserted inside the same instruments. In alternative a special instrument can be created capable of acquiring and elaborating the data.

What is claimed is:

1. System for the automatic evaluation of indexes of volemic status of a patient comprising:

means suitable for submitting said patient to a preset period of apnoea and to a preset period of mechanical breathing;

probes of heart pressure for acquiring an analogical signal relative to the values of the blood pressure of said patient in said preset periods;

an analogue/digital converter for the conversion of said analogical signal into a digital signal;

means to determine the values of positive systolic peaks of said pressure;

means to determine a first average value of the positive systolic peaks of said pressure in said preset period of apnoea;

means to determine a second average value of the maximum positive systolic peaks of said pressure in said preset period of mechanical breathing;

means to determine a third average value of the minimum positive systolic peaks of said pressure in said preset period of mechanical breathing;

means to calculate a first index of volemic status equal to the difference between said second value and said first value;

means to calculate a second index of volemic status equal to the difference between said third value e said first value;

a display of said indexes of volemic status.

2. System in accordance with claim 1 characterised in that said display visualizes an alarm signal if at least one of said indexes of volemic status is outside a preset interval.

3. System in accordance with claim 1 characterised in that said digital signal is filtered by a band-pass filter.

4. Method for evaluating the indexes of volemic status of a patient comprising the following phases:

submitting said patient to a period of preset duration of apnoea;

submitting said patient to a period of preset duration of mechanical breathing;

acquiring the values of the blood pressure of said patient in said preset periods by suitable pressure probes;

determining the values of positive systolic peaks of said pressure;

determining a first average value of the positive systolic peaks of said pressure in said period of apnoea;

determining a second average value of the maximum positive systolic peaks of said pressure in said period of mechanical breathing;

determining a third average value of the minimum positive systolic peaks of said pressure in said period of mechanical breathing;

calculating a first index of volemic status equal to the difference between said second value and said first value;

calculating a second index of volemic status equal to the difference between said third value and said first value;

visualizing said indexes of volemic status on a display.

5. Method in accordance with claim 4 characterised in that a third index of volemic status is calculated equal to the sum of said first index of volemic status and said second index of volemic status.

6. Method in accordance with claim 4 characterised in that if at least one of said indexes of volemic status is outside a preset interval an alarm signal is activated.

7. Method in accordance with claim 4 characterised in that it associates to said period of apnoea a first indicator of beginning of apnoea and a second indicator of end of apnoea.

8. Method in accordance with claim 4 characterised in that it associates to said period of mechanical breathing a first indicator of beginning of mechanical breathing and a second indicator of end of mechanical breathing.

9. Method in accordance with claim 7 characterised in that said phases of associating said indicators to indicator periods of beginning and end is done manually.

10. Method in accordance with claim 7 characterised in that said phases of associating said indicators to indicator periods of beginning and end is done automatically by means of an analysis of the flow of said digital signal.

11. Method in accordance with claim 4 characterised in that the phase of acquiring the pressure values of said patient comes about by receiving the signal supplied by a pressure probe and filtering said signal with a band-pass filter in the interval between 0,5 and 30 Hz.

12. Method in accordance with claim 4 characterised in that the phase of determining the values of positive systolic peaks of said pressure comprises the phases of:

determining the time amplitude of the heart cycle of said patient;

determining the peak value of said pressure within said time amplitude for the first heart cycle;

determining the peak value of said pressure within a preset fraction of said time amplitude positioned centred in the position given by the sum of the time position of the previous positive systolic peak plus said time amplitude.

13. Method in accordance with claim 12 characterised in that it further comprises the phases of:

filtering said values of the blood pressure of said patient with a filter having a pass-band between 0,5 and 3 Hz;

calculating the values of negative peaks of said pressure;

making the average value of said negative peak values;

determining a reference value equal to said average value increased by a preset value;

making a comparison between each single peak determined within said preset amplitude window and said reference value;

if only one peak value is lower than said reference value, the amplitude of said window is increased and the phases of claim 12 are repeated.

* * * * *